United States Patent [19]

Stait

[11] 4,144,885
[45] Mar. 20, 1979

[54] APPARATUS FOR THE DETACHABLE CONNECTION OF A PISTON WITH A PISTON PLUNGER

[75] Inventor: Donald P. Stait, Steinmaur, Switzerland

[73] Assignee: Contraves AG, Zurich, Switzerland

[21] Appl. No.: 820,925

[22] Filed: Aug. 1, 1977

[30] Foreign Application Priority Data

Aug. 31, 1976 [CH] Switzerland ............... 11008/76

[51] Int. Cl.² ............................................. A61M 5/00
[52] U.S. Cl. .................................. 128/218 P; 128/234
[58] Field of Search ......... 128/218 P, 218 PA, 218 R, 128/234, 215

[56] References Cited

U.S. PATENT DOCUMENTS

| Re. 17,059 | 8/1928 | Hein | 128/218 P |
|---|---|---|---|
| 3,164,303 | 1/1965 | Trautmann | 128/218 PA X |
| 3,742,949 | 7/1973 | Hill | 128/218 PA |
| 3,831,601 | 8/1974 | Kessell | 128/218 PA |

*Primary Examiner*—John D. Yasko
*Attorney, Agent, or Firm*—Werner W. Kleeman

[57] ABSTRACT

An apparatus for the detachable connection of an axially to-and-fro movable piston of a syringe with a piston rod or plunger, comprising at least two holder brackets arranged in mutually spaced relationship from one another at the piston plunger and formed of a spring wire, detachably secured with said piston plunger. Each holder bracket essentially comprises two respective axially extending webs and a connection element or piece arranged transversely with respect to said webs. The piston of the syringe possesses a headpiece formed as a substantially truncated cone and equipped with a contact edge engaged by said connection pieces.

4 Claims, 4 Drawing Figures

APPARATUS FOR THE DETACHABLE CONNECTION OF A PISTON WITH A PISTON PLUNGER

BACKGROUND OF THE INVENTION

The present invention relates to a new and improved construction of apparatus for the detachable connection of an axially to-and-fro movable piston of a syringe containing a piston plunger.

According to an injector device, for instance as taught in German patent publication 2,500,851, there is provided, among other things, a holder- and coupling element for two syringes attached to a turret or revolver head, the syringes being pivotable together with the turret head which is rotatably mounted about a pin. The holder- and coupling element arranged between the plunger and the syringe comprises two latching or engaging elements secured to the plunger, these latching elements being provided at the end face as well as at the side walls with a respective appropriately constructed inclined surface. In the position of use, and by virtue of the inclined surfaces, both of the latching elements are forced apart at their end faces and thereafter pushed over an appropriately constructed head of the syringe piston until such engages into an opening provided in each of the latching elements. By rotating the turret head the syringe head pushes apart the side walls which are likewise equipped with an inclined surface, so that the empty syringe can be removed and the second syringe can be brought into a position for use.

SUMMARY OF THE INVENTION

It is a primary object of the present invention to provide a coupling- and holder device between a to-and-fro movable piston rod or plunger and a piston of a syringe with simple means and without any sharp edges and corners and to arrange such in a manner that on the one hand there is ensured for an exact transmission of the traction forces which occur during withdrawal of the piston out of the syringe, with maximum operational reliability, and, on the other hand, during insertion of the piston into the syringe to enable the occurring thrust forces to act directly upon the piston, and wherein, additionally the coupling- and holder device allows for an axial coupling and radial decoupling without any particular expenditure in force.

Another significant object of the present invention aims at the provision of a new and improved construction of apparatus for the detachable connection of a piston with a piston plunger or rod in an extremely reliable and positive fashion, which apparatus is relatively simple in construction and design, and economical to fabricate.

Now in order to implement these and still further objects of the invention, which will become more readily apparent as the description proceeds, the apparatus of this development is manifested by the features that at least two holder brackets are detachably secured to the piston plunger in spaced relationship from one another and are each formed of a steel spring wire. Each of the holder brackets comprises two axially extending webs and a connection piece or element arranged transversely with respect to said webs. The piston of the syringe possesses a headpiece formed substantially as a truncated cone and equipped with a contact edge.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
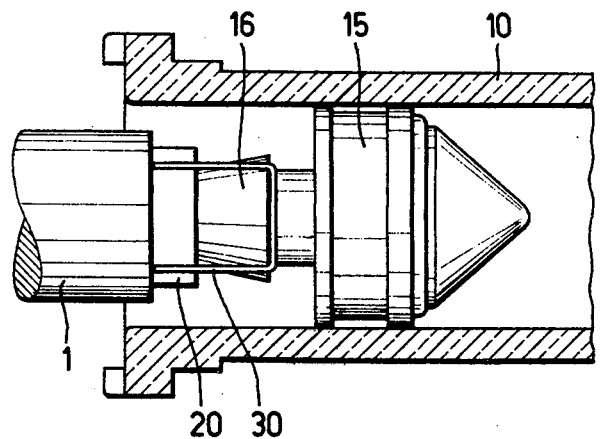
FIG. 1 is a fragmentary sectional view of a syringe showing a partially inserted piston.

Describing now the drawings, in FIG. 1 there is shown in sectional view a cylinder 10 of a syringe in which there can be moved to-and-fro a piston 15 which is detachably connected with a piston plunger or rod 1, this piston plunger or rod being actuated by a not particularly illustrated injector head.

Figure 2:
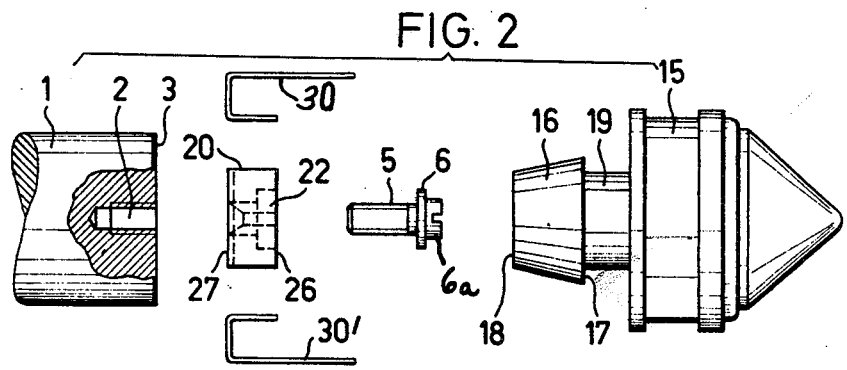
FIG. 2 is an exploded view showing details of the connection- and coupling location of the piston with the piston plunger or rod.

FIG. 2 shows in exploded view the connection- and coupling location and there will be seen the piston rod or plunger 1, the piston 15 and the coupling-connection elements composed of a clamping piece or element 20, two coupling brackets 30 and 30' and an attachment screw 5.

The piston 15 is provided at the side facing away from the medium which is to be injected with a headpiece 16 which is formed at an intermediate piece 19 of a not further illustrated inner part of the piston 15. The headpiece 16 is constructed substantially in the form of a truncated cone and has an end face or surface 18 formed as a contact surface as well as a substantially annular or ring-shaped contact edge 17.

The piston rod or plunger 1 is equipped with a threaded hole or aperture 2 which is axially inwardly directed from its end face 3. This threaded hole 2 serves for receiving the screw 5 by means of which the clamping element 20 is attached to the end face 3 of the piston plunger 1.

Figure 3:
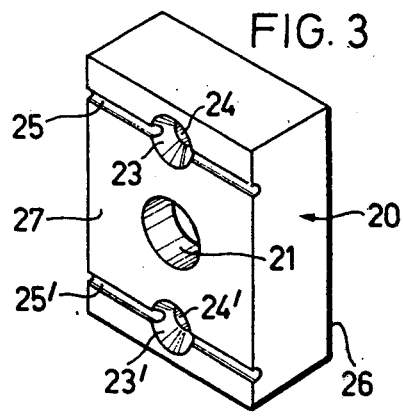
FIG. 3 is a perspective, enlarged view of a clamping element.

In FIG. 3 there is shown in perspective and enlarged view the clamping element or piece 20. At the rear side or face 27 of the clamping element 20 there are provided two mutually spaced centering openings 23 and 23' which are preferably of conical construction, each of which open into a correspondingly arranged throughpass bore 24 and 24' respectively. Channel- or spline-shaped constructed grooves 25 and 25' are provided over the entire width of the rear face or surface 27 and extend from the openings 23, 23' up to the outer edge of the clamping element 20, as shown. At the center the clamping element 20 additionally possesses a throughpass bore 21 which opens into a recess 22 arranged at the end face 26 and which is matched to the outer diameter of the screw head 6a. The depth of the recess 22 is dimensioned such that a disk 6 as well as the head 6a of the screw 5 does not outwardly protrude in the assembled condition of the arrangement.

Figure 4:
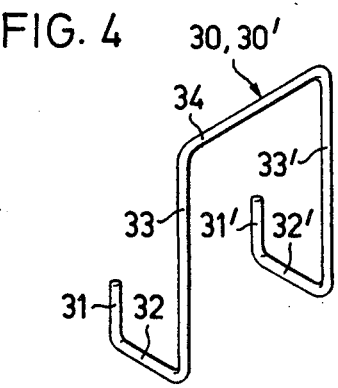
FIG. 4 is a perspective and enlarged view of a coupling bracket.

Now in FIG. 4 there is shown in a perspective and enlarged view the coupling- and holder brackets 30 and 30', each of which comprise a horizontally extending connection element 34, two laterally therewith merging, rectangularly bent-out and downwardly directed webs or legs 33 and 33', two bent portions 32 and 32' merging with the webs 33 and 33' and extending transverse to the connection element 34 as well as two therewith merging ends 31 and 31' which extend essentially parallel to the webs 33 and 33'. In order that the holder bracket, in the assembled condition, possesses a slight pre-stress, the webs 33 and 33' can be slightly bent at an inclination with respect to the bent portions 32 and 32' according to a not particularly illustrated variant embodiment. Each holder bracket 30 and 30' is formed for instance of a steel spring wire.

During assembly of the parts 1, 20 and 30, 30' both of the ends 31 and 31' of the holder bracket are inserted into the appropriately dimensioned holes 24 and 24' of the clamping piece or element 20, whereas the bent portions 32 and 32' are located in the grooves 25 and 25'. The depth of the grooves 25 and 25' is dimensioned such that the wire thickness of the holder brackets flushly merges with the rear face 27, but preferably is however located somewhat lower. By means of the screw 5 or equivalent structure the clamping element 20 is attached at its rear face 27 at the end face or surface 3 of the rod or plunger 1, so that the plunger, the holder brackets 30 and 30', as well as the clamping element 20 form a unit. The spacing of both holder brackets 30 and 30' from one another is dimensioned such that the truncated cone-shaped constructed headpiece 16 spreads the holder brackets apart somewhat during connection of the piston rod or plunger 1 with the piston 15, and which holder brackets thereafter latch or engage by means of the connection elements or pieces 34 in a cliplike fashion behind the contact edge 17 of the headpiece.

During the injection operation the piston rod or plunger 1 which is actuated by a not particularly illustrated injector head together with the clamping element 20 presses against the end face or surface 18 of the piston-headpiece 16, whereas during axial retraction of the piston 15 the holder brackets 30 and 30' which are latched or engage behind the headpiece 16 serve as the coupling- and entrainment element. As soon as the syringe has been axially withdrawn to a location where there is freed the plunger 1 and the headpiece 20, then the cylinder 10 together with the piston 15 can be radially removed out of the holder brackets 30 and 30'.

The described apparatus fulfils the requirement of providing a coupling-like detachable connection between an axial to-and-fro movable piston rod or plunger 1 and a piston 15 of a syringe, without the need for any special expenditure in equipment and with the greatest operational reliability. In particular, there is possible simple assembly and disassembly in an optimum way of the parts or components which are to be cleaned periodically, without danger of damaging the same.

While there are shown and described present preferred embodiments of the invention, it is to be distinctly understood that the invention is not limited thereto, but may be otherwise variously embodied and practiced within the scope of the following claims. ACCORDINGLY,

What I claim is:

1. An apparatus for the detachable connection of an axial to-and-fro movable piston of a syringe with a piston plunger, comprising:
    at least two holder brackets arranged in spaced relationship from one another and detachably secured with the piston plunger;
    each of said holder brackets being formed of a spring wire;
    each of said holder brackets comprising two respective essentially axially extending webs and a connection element arranged transversely with respect to said webs;
    a headpiece constructed in the form of a substantially truncated conical member provided for the piston of the syringe; and
    said headpiece having a contact edge with which engage said connection elements.

2. The apparatus as defined in claim 1, further including:
    a clamping element for securing the holder brackets with an end face of the piston plunger.

3. The apparatus as defined in claim 1, wherein:
    a respective bent-off portion is provided at the webs of the holder brackets and merging therewith end portions extending substantially parallel to said webs.

4. The apparatus as defined in claim 2, wherein:
    said clamping element has a rear face provided with two spaced bores for the reception of the end portions and grooves for the reception of the bent-off portions of the holder bracket.

* * * * *